United States Patent
Majeed et al.

(10) Patent No.: US 10,792,295 B2
(45) Date of Patent: Oct. 6, 2020

(54) COMPOSITIONS FOR MANAGEMENT OF HELICOBACTER PYLORI INFECTIONS

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(73) Assignee: SAMI LABS LIMITED, Bangalore (IN)

( * ) Notice: Subject to any disclaimer, the term of this patent is extended or adjusted under 35 U.S.C. 154(b) by 136 days.

(21) Appl. No.: 16/001,096

(22) Filed: Jun. 6, 2018

(65) Prior Publication Data

US 2018/0344754 A1 Dec. 6, 2018

Related U.S. Application Data

(60) Provisional application No. 62/516,066, filed on Jun. 6, 2017.

(51) Int. Cl.
*A61K 31/7024* (2006.01)
*A61P 31/04* (2006.01)
*A61K 35/742* (2015.01)

(52) U.S. Cl.
CPC ........ *A61K 31/7024* (2013.01); *A61K 35/742* (2013.01); *A61P 31/04* (2018.01)

(58) Field of Classification Search
CPC .... A61K 31/7024; A61K 35/742; A61P 31/04
USPC ..................................................... 424/93.46
See application file for complete search history.

(56) References Cited

FOREIGN PATENT DOCUMENTS

CN 103565848 * 2/2017

OTHER PUBLICATIONS

Chung et al., Inhibitory Actions of Emodin on Arylamine N-Acetyltransferase Activity in Strains of Helicobacter pylori from Peptic Ulcer Patients, Food and Chemical Toxicity, 35, (1997), pp. 1001-1007.*

Imtiyaz et al., Pistacia lentiscus Linn.: Gum with immense medicinal Potential, Spatula DD., vol. 3, Iss. 2, (2013), pp. 69-73.*
Majeed et al., Evaluation of genetic and phenotypic consistency of Bacillus coagulans MTCC 5856: a commercial probiotic strain, World Journal of Microbiology and Biotechnology, vol. 32, Iss. 60, (2016), pp. 1-12.*
Chung et al., Inhibitory actions of ellagic acid on growth and arylamine N-acetyltransferase activity in strains of Helicobacter pylori from peptic ulcer patients, Microbios., vol. 93, No. 375, (1998), pp. 115-127; Abstract presented.*
Helicobacter pylori (H. pylori) infection, https://www.mayoclinic.org/diseases-conditions/h-pylori/symptoms-causes/syc-20356171, accessed May 1, 2018.
Taylor et al., (1991). The Epidemiology of Helicobacter pylori Infection, Epidemiologic Reviews 13(1):42-59.
Parsonnet et al., (1991). Helicobacter pylori Infection and the Risk of Gastric Carcinoma, N Engl J Med 325:1127-1131.
Kusters et al., (2006). Pathogenesis of Helicobacter pylori Infection, Clinical Microbiology Reviews, 19(3):449-490.
Bonifácio et al., (2014). Antimicrobial activity of natural products against Helicobacter pylori: a review, Ann Clin Microbiol Antimicrob, 13:54.
Vetvika et al., (2016). Effects of curcumin on Helicobacter pylori infection, Ann Transl Med. 4(24): 479.
Hajimahmoodi et al., (2011). In vitro antibacterial activity of some Iranian medicinal plant extracts against Helicobacter pylori, Natural Product Research, 25(11):1059-1066.
Tharmalingam et al., (2014). Inhibitory effect of piperine on Helicobacter pylori growth and adhesion to gastric adenocarcinoma cells, Infect Agent Cancer, 9: 43.
Wang et al., (2014) The clinical trial on the eradication of Helicobacter pylori using Bacillus coagulans tablets and triple therapy, Chinese Journal of Microecology, Apr. 2013, http://en.cnki.com.cn/Article_en/CJFDTOTAL-ZGWS201304014.htm, accessed May 24, 2018).
Probiotics: In Depth/NCCIH, U.S. Department of Health and Human Services, National Institutes of Health.

* cited by examiner

*Primary Examiner* — Jennifer M. H. Tichy

(57) ABSTRACT

Disclosed are compositions containing at least 10% w/w or above of 1-O-galloyl-β-D-glucose (β-glucogallin) which additionally comprising of about 10% w/w to greater than 60% w/w total mucic acid gallates including mucic acid 1,4-lactone 5-O-gallate, mucic acid 2-O-gallate, mucic acid 6-Methyl ester 2-O-gallate, mucic acid 1-Methyl ester 2-O-gallate and ellagic acid, and a probiotic bacteria *Bacillus coagulans* MTCC 5856, individually or in combination for inhibiting the growth and managing infections of *Helicobacter pylori*.

16 Claims, 2 Drawing Sheets

COMPOSITIONS FOR MANAGEMENT OF HELICOBACTER PYLORI INFECTIONS

CROSS-REFERENCE TO RELATED APPLICATIONS

This is a non-provisional application claiming priority of U.S. provisional application No. 62/516,066, filed on 6 Jun. 2017.

BACKGROUND OF THE INVENTION

Field of the Invention

The invention in general relates to anti-microbial compositions. More specifically, the present invention relates to the management of *Helicobacter pylori* infections using a composition containing probiotic bacteria *Bacillus coagulans* MTCC 5856 and β-glucogallin.

Description of Prior Art

*Helicobacter pylori* is a bacterium that infects the stomach lining and is responsible for majority of stomach and intestinal ulcers. Although present in more than half of the world's population, most do not realize that they suffer from *H. pylori* infections and do not show any symptoms due to their innate resistance to *H. pylori*. If symptoms are realized, they are presented with gastritis, ache or burning pain in abdomen, nausea, loss of appetite, frequent burping, bloating, bad breath and unintentional weight loss. *H. pylori* is associated with many disease states which include epidemic gastritis, hypochlorhydria, gastroduodenal inflammation, ulcers, dyspepsia, gastric carcinoma and lymphoma, Gastroesophageal reflux disease and Extragastroduodenal disorders like coronary heart disease, dermatological disorders such as rosacea and idiopathic urticaria, autoimmune thyroid disease and thrombocytopenic purpura, iron deficiency anemia, Raynaud's phenomenon, scleroderma, migraine, and Guillain-Barré syndrome.

The following prior art documents discusses in detail the infections and pathogenesis of *H. pylori*:
1. *Helicobacter pylori* (*H. pylori*) infection, https://www-.mayoclinic.org/diseases-conditions/h-*pylori*/symptoms-causes/syc-20356171, accessed 1 May 2018.
2. Taylor et al., (1991). The Epidemiology of *Helicobacter pylori* Infection, *Epidemiologic Reviews* 13(1):42-59,
3. Parsonnet et al., (1991). *Helicobacter pylori* Infection and the Risk of Gastric Carcinoma, N Engl J Med 325:1127-1131
4. Kusters et al., (2006). Pathogenesis of *Helicobacter pylori* Infection, Clinical Microbiology Reviews, 19(3):449-490.

The current treatment for *H. pylori* involve triple therapies which include omeprazole, amoxicillin, and clarithromycin (OAC) for 10 days; bismuth subsalicylate, metronidazole, and tetracycline (BMT) for 14 days; and lansoprazole, amoxicillin, and clarithromycin (LAC), which has been approved for either 10 days or 14 days of treatment. However, just like other treatment methods, the drugs administered to treat *H. pylori* infections exhibit side effects which include diarrhea, headache, nausea, vomiting, stomach pain, unusual or unpleasant taste in your mouth, constipation, dark colored stools, dry mouth, increased thirst, vaginal itching or discharge. Hence there exists a need to find a safe and reliable alternative. Currently research is on identifying natural molecules that are effective against *H. pylori* infections. The following prior art documents report the role of natural molecules in the prevention and treatment of *H. pylori* infections:
1. Bonifácio et al., (2014). Antimicrobial activity of natural products against *Helicobacter pylori*: a review, Ann Clin Microbiol Antimicrob, 13:54.
2. Vetvika et al., (2016). Effects of curcumin on *Helicobacter pylori* infection, Ann Transl Med. 4(24): 479.
3. Hajimahmoodi et al., (2011). In vitro antibacterial activity of some Iranian medicinal plant extracts against *Helicobacter pylori*, Natural Product Research, 25(11):1059-1066.
4. Tharmalingam et al., (2014). Inhibitory effect of piperine on *Helicobacter pylori* growth and adhesion to gastric adenocarcinoma cells, Infect Agent Cancer, 9: 43.

Probiotic bacteria is also reported to inhibit the growth of *H. pylori* in combination with triple therapy (Wang et al., (2014) The clinical trial on the eradication of *Helicobacter pylori* using *Bacillus coagulans* tablets and triple therapy, Chinese Journal of Microecology, 2013-04, http://en.cnki.com.cn/Article_en/CJFDTOTAL-ZGWS201304014.htm, accessed 24 May 2018).

A safe and reliable natural molecule that is effective against most strains of *H. pylori* is lacking. Additionally, a probiotic strain that can be used in the treatment of *H. pylori* infections as a standalone is also warranted. Moreover, it is well known in the scientific art that biological effects of probiotics or products thereof are strain specific and cannot be generalised among genera, species and strains (Probiotics: In Depth/NCCIH, U.S. Department of Health and Human Services, National Institutes of Health). Hence, there exists a need to find a superior probiotic strain, its extracellular product and/or a natural plant molecule that can be used effectively for the management of *H. pylori* infections. The present invention solves the above problem by disclosing a novel and non-obvious composition containing β glucogallin and a probiotic bacteria *Bacillus coagulans* MTCC 5856, individually or in combination for the management of *H. pylori* infections.

It is the principle objective of the invention to disclose a composition containing β glucogallin and *Bacillus coagulans* MTCC 5856 for inhibiting the growth of *H. pylori*

It is another objective of inventions to disclose a composition containing β glucogallin and *Bacillus coagulans* MTCC 5856 for the management of *H. pylori* infections.

The present invention fulfils the above aspects and provides further related advantages.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh-160036, India.

SUMMARY OF THE INVENTION

The present invention discloses a compositions containing compositions containing at least 10% w/w or above of 1-O-galloyl-β-D-glucose (β-glucogallin) which additionally comprising of about 10% w/w to greater than 60% w/w total mucic acid gallates including mucic acid 1,4-lactone 5-O-gallate, mucic acid 2-O-gallate, mucic acid 6-Methyl ester 2-O-gallate, mucic acid 1-Methyl ester 2-O-gallate and ellagic acid, and a probiotic bacteria *Bacillus coagulans*

MTCC 5856, individually or in combination for the inhibiting the growth and managing infections of *Helicobacter pylori*.

DESCRIPTION OF THE MOST PREFERRED EMBODIMENTS

Figure 1:
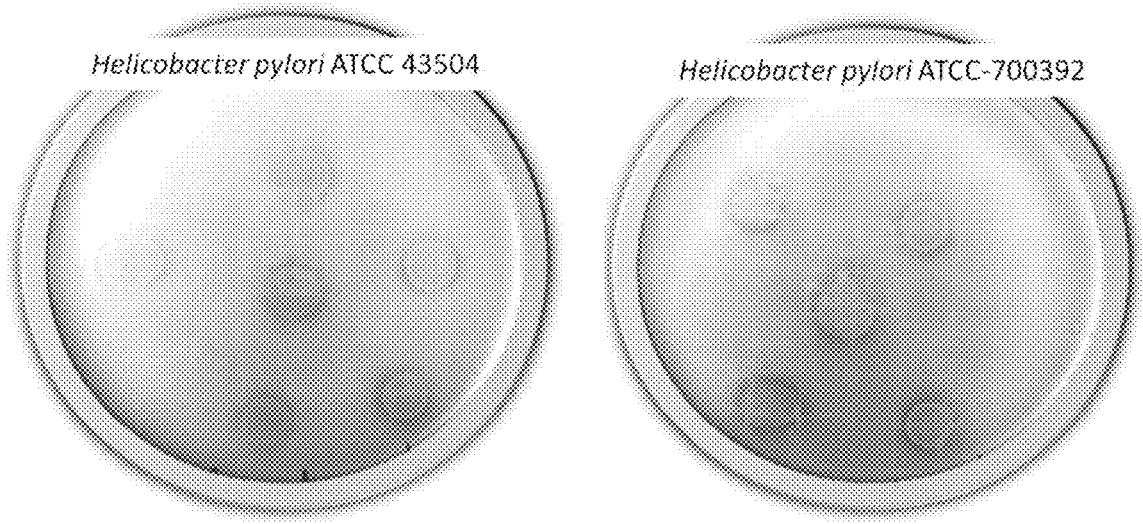
FIG. 1 is the image of culture plates showing the antibacterial activity of *B. coagulans* MTCC 5856 against *H. pylori* ATCC 43504 and ATCC 700392 by following spot in lawn method

In a most preferred embodiment, the present invention discloses a method of inhibiting the growth of *Helicobacter pylori* strains, said method comprising steps of bringing into contact *Helicobacter pylori* strains with a composition containing a) at least 10% w/w or above of 1-O-galloyl-β-D-glucose (β-glucogallin) and 10% w/w to greater than 60% w/w total mucic acid gallates, b) effective dose of probiotic bacteria *Bacillus coagulans*, individually or in combination, to inhibit the growth of *Helicobacter pylori*. In a related embodiment, the strains of *H. pylori* include *Helicobacter pylori* ATCC 43504 and *Helicobacter pylori* ATCC 700392. In another related embodiment the mucic acid gallates are selected from the group consisting of mucic acid 1,4-lactone 5-O-gallate, mucic acid 2-O-gallate, mucic acid 6-Methyl ester 2-O-gallate, mucic acid 1-Methyl ester 2-O-gallate and ellagic acid. In yet another related embodiment, the *Bacillus coagulans* strain is preferably *Bacillus coagulans* MTCC 5856. In an embodiment, the effect dose of *Bacillus coagulans* is $1 \times 10^6$ to $1 \times 10^{14}$ colony forming units per unit dose. In another related embodiment, the effective dose of *Bacillus coagulans* is preferably $2 \times 10^9$ colony forming units per unit dose.

In another most preferred embodiment, the present invention discloses a method of therapeutic management of symptoms and infections of *Helicobacter pylori* strains in mammals, said method comprising steps of administering a composition containing a) at least 10% w/w or above of 1-O-galloyl-β-D-glucose (β-glucogallin) and 10% w/w to greater than 60% w/w total mucic acid gallates, b) effective dose of probiotic bacteria *Bacillus coagulans*, individually or in combination, to said mammals, to bring about a reduction in the symptoms and infections of *Helicobacter pylori*. In a related embodiment, the strains of *H. pylori* include *Helicobacter pylori* ATCC 43504 and *Helicobacter pylori* ATCC 700392. In another related embodiment the mucic acid gallates are selected from the group consisting of mucic acid 1,4-lactone 5-O-gallate, mucic acid 2-O-gallate, mucic acid 6-Methyl ester 2-O-gallate, mucic acid 1-Methyl ester 2-O-gallate and ellagic acid. In yet another related embodiment, the *Bacillus coagulans* strain is preferably *Bacillus coagulans* MTCC 5856. In an embodiment, the effect dose of *Bacillus coagulans* is $1 \times 10^6$ to $1 \times 10^{14}$ colony forming units per unit dose. In another related embodiment, the effective dose of *Bacillus coagulans* is preferably $2 \times 10^9$ colony forming units per unit dose. In another related embodiment, the symptoms of *H. pylori* infections are selected from the group consisting of gastritis, ache or burning pain in abdomen, nausea, loss of appetite, frequent burping, bloating, bad breath and unintentional weight loss. In yet another related embodiment, infections of *H. pylori* strains are selected from the group consisting of epidemic gastritis, hypochlorhydria, gastroduodenal inflammation, ulcers, dyspepsia, gastric carcinoma and lymphoma, Gastroesophageal reflux disease and Extragastroduodenal disorders like coronary heart disease, dermatological disorders such as rosacea and idiopathic urticaria, autoimmune thyroid disease and thrombocytopenic purpura, iron deficiency anemia, Raynaud's phenomenon, scleroderma, migraine, and Guillain-Barré syndrome In a related embodiment, the composition is formulated with pharmaceutically/nutraceutically acceptable excipients, adjuvants, diluents or carriers and administered in the form of tablets, capsules, syrups, gummies, powders, suspensions, emulsions, chewables, candies and eatables. In another aspect, the composition containing β-glucogallin and/or *Bacillus coagulans* MTCC 5856 is administered as a stand alone or in combination with the standard drugs used for treating *H. pylori* infections (triple therapy—which include omeprazole, amoxicillin, and clarithromycin (OAC) for 10 days; bismuth subsalicylate, metronidazole, and tetracycline (BMT) for 14 days; and lansoprazole, amoxicillin, and clarithromycin (LAC), which has been approved for either 10 days or 14 days of treatment). In an embodiment, the mammal is preferably human.

Specific illustrative examples enunciating the most preferred embodiments are included herein below.

Example 1: Anti-*Helicobacter pylori* Activity of β Glucogallin and *Bacillus coagulans*

Methods: Bacterial Strains and Growth Conditions

*Helicobacter pylori* ATCC 43504 and ATCC 700392 were purchased from the American Type Culture Collection (ATCC, Manassas, Va., USA). Cultures were grown in brain heart infusion (BHI) agar/broth (HiMedia, Mumbai India) supplemented with 7% (v/v) sheep blood or fetal bovine serum and incubated at 37° C. under microaerobic conditions (Na, 85%; 02, 5%; $CO_2$, 10%) using an anaerobic chamber (Imset, Mumbai, India). *Bacillus coagulans* MTCC 5856 was grown in MRS media by adding inoculum (5% v/v) to the MRS broth and incubated at 37° C. for 24 h. After 24 h, the culture was centrifuged (5,000×g) to remove the cells and the supernatant was collected, concentrated 10-fold by lyophilization and filter sterilized through a 0.22 micron filter (Millipore, India). The cell-free supernatant was tested against *H. pylori* and 10-fold concentrated supernatant was also tested against *H. pylori* ATCC 43504 and ATCC 700392.

Antibacterial Activity Test

Spot On-Lawn Method

Freshly grown cultures of *Helicobacter pylori* ATCC 43504 and ATCC 700392 were added to the brain heart infusion (BHI) agar (HiMedia, Mumbai India) supplemented with 7% (v/v) fetal bovine serum, and approximately 20 ml of this suspension was added to the Petri dish and allowed to solidify in the plates. Further, overnight grown culture of *B. coagulans* MTCC 5856 (50 µl) was spotted onto the top of agar plate containing *Helicobacter pylori* ATCC 43504 or ATCC 700392. Plates were dried at room temperature and then incubated at 37° C. under microaerobic conditions (Na, 85%; $O_2$, 5%; $CO_2$, 10%) using an anaerobic chamber (Imset, Mumbai, India) for 3 days.

Well Diffusion Method

Similar to above, BHI agar plates supplemented with 7% (v/v) fetal bovine serum were prepared containing a strain of

*Helicobacter pylori* ATCC 43504 or ATCC 700392. Further, well was made in the BHI agar plates containing *Helicobacter pylori* ATCC 43504 or ATCC 700392. 100 µl of *B. coagulans* supernatant (overnight grown) or 10-fold concentrated supernatant of the same was added to the each well. Similarly, 100 µl containing the concentration of curcumin, β-glucogallin and mucic acid gallates and Piperine were added to each plate. Plates were incubated at 37° C. under microaerobic conditions (Na, 85%; 02, 5%; $CO_2$, 10%) using the anaerobic chamber (Imset, Mumbai, India) for 3 days. After incubation, the antibacterial activities were evaluated by measuring a diameter of the inhibition zone. Experiment was repeated twice in duplicate and average mean of zone of inhibition is expressed in millimetres.

Minimum Inhibitory Concentration (MIC) Determination

The MICs of curcumin, β-glucogallin and mucic acid gallates extract and Piperine extract were determined as per the guidelines of Clinical and Laboratory Standards Institute (formerly the National Committee for Clinical Laboratory Standards). Briefly, the bacterial suspensions (*Helicobacter pylori* ATCC 43504 and ATCC 700392) were prepared by suspending 72 h grown bacterial culture in sterile normal saline (0.89% NaCl w/v). The turbidity of the bacterial suspension was adjusted to 0.5 McFarland standards (equivalent to $1.5 \times 10^8$ colony forming units (CFU)/ml). Curcumin, β-glucogallin and mucic acid gallates and Piperine extract stock solutions were prepared in 100% dimethyl sulfoxide (DMSO; Merck, Mumbai, India) and 2-fold serial dilutions were prepared in brain heart infusion (BHI) broth (HiMedia, Mumbai India) supplemented with 7% (v/v) fetal bovine serum (FBS) in 100 µl volume in 96-well U bottom microtiter plates (Tarson, Mumbai India). The above-mentioned bacterial suspension was further diluted in the BHI-FBS and 100 µl volume of this diluted inoculum was added to each well of the plate resulting in the final inoculum of $1 \times 10^6$ CFU/ml in the well and the final concentration of curcumin, β-glucogallin and mucic acid gallates extract and Piperine extract ranged from 3.9 to 2000 µg/ml. The plates were incubated at 37° C. for 72 h under micro-aerobic conditions of 5% $O_2$, 10% $CO_2$, and 85% $N_2$ gas mixture (Imset, Mumbai India) for 72 h. After incubation, plates were visually read for the absence or presence of turbidity. The minimum concentration of the compound concentration showing no turbidity was recorded as MIC.

Results

The anti-microbial activity of β glucogallin and *Bacillus coagulans* MTCC 5856 against *H. pylori* was evaluated in addition to the other well known anti-*H. pylori* agents. The results are tabulated in table 1.

The results indicated that both β-glucogallin and mucic acid gallates, and the probiotic bacteria inhibited the growth of *Helicobacter pylori*, and can be used as effective agents for the treatment of *H. pylori* infections.

The MIC values of the plant extracts (table 2) also indicated that β-glucogallin and mucic acid gallates showed a significant inhibition in the growth of *H. pylori* with MIC values of 1000-2000 (µg/ml) for both the strains of *H. pylori*.

TABLE 2

Antibacterial activity (minimum inhibitory concentration, MIC) of samples against pathogen *Helicobacter pylori*.

| | | MIC range (µg/ml) | |
|---|---|---|---|
| S. No. | Sample | *H. pylori* ATCC 43504 | *H. pylori* ATCC 700392 |
| 1 | Curcumin | 125 to 250 | 125 to 250 |
| 2 | Piperine extract | 1000 to 2000 | 1000 to 2000 |
| 3 | β-glucogallin and mucic acid gallates | 1000 to 2000 | 1000 to 2000 |

Figure 2:
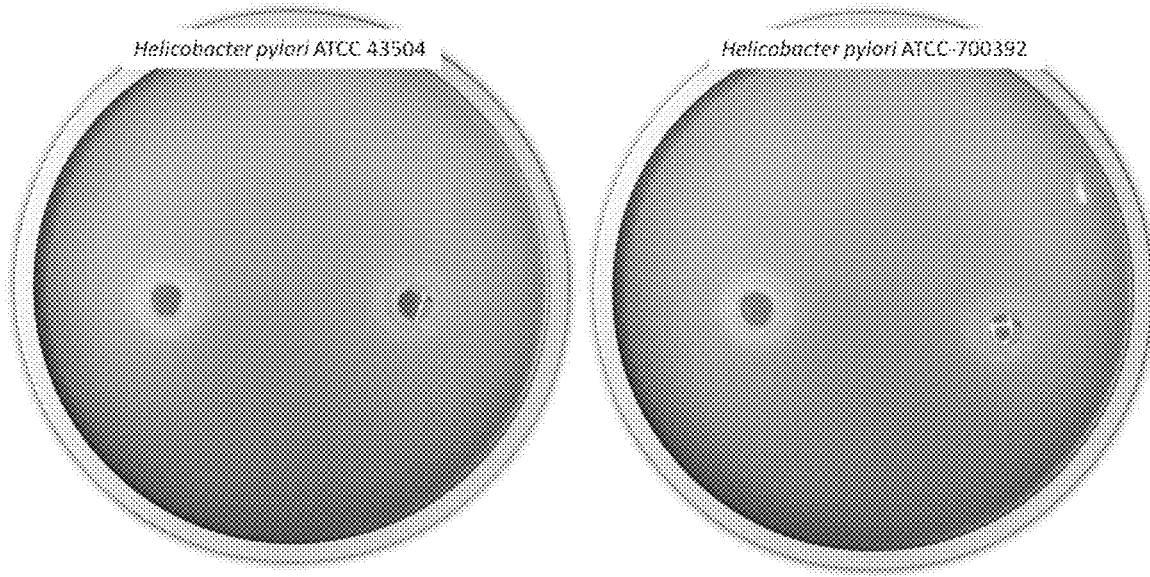
FIG. 2 is the image of culture plates showing the antibacterial activity of *B. coagulans* MTCC 5856 against *H. pylori* ATCC 43504 and ATCC 700392 by following well diffusion method.
Figure 3:
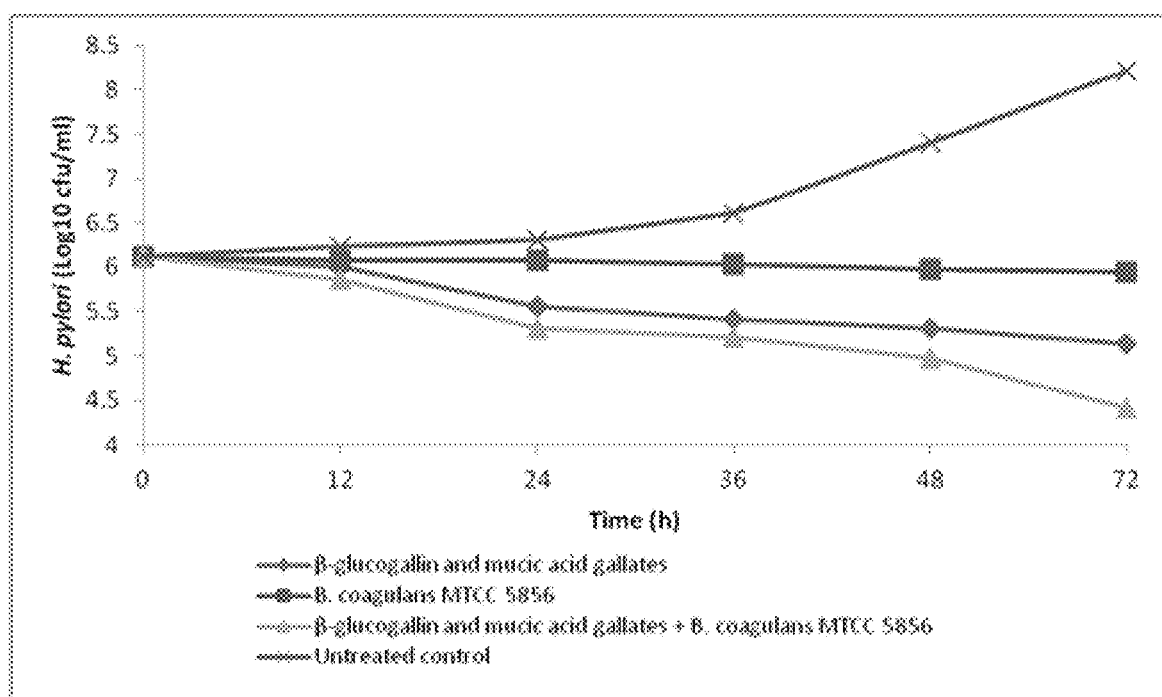
FIG. 3 is the graphical representation showing the inhibition in growth of *H. pylori* by a combination containing *B. coagulans* MTCC 5856 and β glucogallin

The anti-bacterial activity of *Bacillus coagulans* MTCC 5856 against *H. pylori* by spot in lawn method (FIG. 1) and well diffusion method (FIG. 2) revealed that the probiotic bacteria inhibited the growth of *H. pylori* and may be included in compositions for the therapeutic management of *H. pylori* infections.

Example 2: Synergistic Anti-*Helicobacter pylori* Activity of Composition Containing β Glucogallin and *Bacillus coagulans* MTCC 5856

The synergistic activity of the combination containing β glucogallin and *Bacillus coagulans* MTCC 5856 was also evaluated.

Combination Study

The bacterial suspension of *Helicobacter pylori* strains (ATCC 43504 and ATCC 700392) was prepared by suspending 72 h grown bacterial culture in sterile normal saline (0.89% NaCl w/v). The turbidity of the bacterial suspension was adjusted to 0.5 McFarland standards (equivalent to $1.5 \times 10^8$ colony forming units (CFU)/ml). 1 ml of this bacterial suspension was added to 100 ml tryptic soya broth containing 10% fetal bovine serum, 5 g/L yeast extract and 2.5 g/L of bacteriological peptone. Further, 5 ml of overnight grown culture of *B. coagulans* MTCC 5856 was added to the each flask. Similarly, different concentrations of β-glucogallin and mucic acid gallates were added to these flasks with and without *B. coagulans* MTCC 5856. Respective controls

TABLE 1

Antibacterial activity (zones of inhibition, mm) of the probiotic bacteria *B. coagulans* MTCC 5856 and other plant extracts against pathogen *Helicobacter pylori*

| | | | Zones of inhibition (mm) | |
|---|---|---|---|---|
| S. No. | Samples | Concentrations (µg/well) | *H. pylori* ATCC 43504 | *H. pylori* ATCC 700392 |
| 1 | Curcumin | 1000 | 13 ± 1.2 | 14 ± 1.2 |
| 2 | Piperine extract | 1000 | 12 ± 1.5 | 13 ± 1.2 |
| 3 | β-glucogallin and mucic acid gallates | 1000 | 11 ± 1.1 | 10 ± 1.2 |
| 4 | *B. coagulans* MTCC 5856 | 100 | 8 ± 1.6 | 9 ± 1.2 |
| 5 | *B. coagulans* MTCC 5856 (10-fold concentrated) | 100 | 13 ± 1.4 | 14 ± 1.2 | were taken in the study. All the flask were incubated at 37° C. for 72 h under micro-aerobic conditions of 5% O2, 10% CO$_2$, and 85% N$_2$ gas mixture (Imset, Mumbai India) for 72 h. After incubation, viable count of *H. pylori* was determined using serial dilution method on BHI agar plates supplemented with 10 mg/L vancomycin, 5 mg/L trimethoprim, and 3500 U polymyxin B/L. Experiments were performed in duplicate and repeated twice. Results are expressed in mean log 10 cfu/ml of *H. pylori*.

Results

Results of the study clearly revealed that in combination of β-glucogallin and mucic acid gallates and probiotic strain *B. coagulans* MTCC 5856 were effective in inhibiting *H. pylori* growth after 72 of incubation. Further, *B. coagulans* MTCC 5856 alone was also effective in inhibiting the *H. pylori* growth but in combination with β-glucogallin and mucic acid gallates, the effectiveness was significantly better than individual, indicating the synergistic effect of the composition.

Example 3: Formulations Containing β Glucogallin and *Bacillus coagulans* for Management of *Helicobacter pylori* Infections Tables 3-8, provides illustrative examples of formulations containing *Bacillus coagulans* and β-glucogallin for management of *Helicobacter pylori* infections

TABLE 3

β-glucogallin and *Bacillus coagulans* Tablet

| Active Ingredients |
| --- |
| β-glucogallin and mucic acid gallates (50-500 mg)<br>*Bacillus coagulans* MTCC 5856: 2 billion cfu<br>Plant fiber<br>Excipients |
| Microcrystalline cellulose, Hypromellose, Croscarmellose Sodium, Colloidal silicon dioxide, Magnesium stearate |

TABLE 4

β-glucogallin and *Bacillus coagulans* Tablet

| Active Ingredients |
| --- |
| β-glucogallin and mucic acid gallates (50-500 mg)<br>*Bacillus coagulans* MTCC 5856: 2 billion cfu<br>Plant fiber, Bioperine ® (Piperine extract),<br>Curcumin C$^3$ Complex ® (Curcumin Extract)<br>Excipients |
| Microcrystalline cellulose, Hypromellose, Croscarmellose Sodium, Colloidal silicon dioxide, Magnesium stearate |

®Registered TM of Sabinsa Corporation

TABLE 5

β-glucogallin and *Bacillus coagulans* Capsule

| Active Ingredients |
| --- |
| β-glucogallin and mucic acid gallates (50-500 mg)<br>*Bacillus coagulans* MTCC 5856: 2 billion cfu<br>Excipients |
| Microcrystalline cellulose, Croscarmellose Sodium, Magnesium stearate |

®Registered TM of Sabinsa Corporation

TABLE 6

β-glucogallin and *Bacillus coagulans* Capsule

| Active Ingredients |
| --- |
| β-glucogallin and mucic acid gallates (50-500 mg)<br>*Bacillus coagulans* MTCC 5856: 2 billion cfu<br>Plant fiber, Bioperine ® (Piperine extract),<br>Curcumin C$^3$ Complex ® (Curcumin Extract)<br>Excipients |
| Microcrystalline cellulose, Croscarmellose Sodium, Magnesium stearate |

®Registered TM of Sabinsa Corporation

TABLE 7

Gummy composition

| Active Ingredients |
| --- |
| β-glucogallin and mucic acid gallates (50-500 mg),<br>*Bacillus coagulans* MTCC 5856: 2 billion cfu<br>Pectin, Glucose corn syrup<br>Excipients |
| Citiric acid, Lactic acid, Lemon peel oil (flavor), DL Tartaric acid, refinated sugar |

TABLE 8

Digestive Premix containing β-glucogallin and *Bacillus coagulans*

| Active Ingredients |
| --- |
| β-glucogallin and mucic acid gallates (50-500 mg),<br>*Bacillus coagulans* MTCC 5856,<br>Fenumannans, Triphala Aquasol, 20% Gingerols,<br>Excipients |
| Maltodextrin, Citric Acid, Malic Acid, Sucralose, Lime, Spearmint and Mangoginger flavours and artificial Mint Flavour, Cumin powder, Black Salt powder, Asafoetida |

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of inhibiting growth of *Helicobacter pylori* strains, said method comprising bringing into contact *Helicobacter pylori* strains with a composition containing:
    a) at least 10% w/w 1-O-galloyl-β-D-glucose (β-glucogallin) and at least 10% w/w total mucic acid gallates, and
    b) an effective dose of probiotic bacteria *Bacillus coagulans*, thereby, inhibiting the growth of *Helicobacter pylori*.

2. The method as in claim 1, wherein the strains of *H. pylori* include *Helicobacter pylori* ATCC 43504 and *Helicobacter pylori* ATCC 700392.

3. The method as in claim 1, wherein the mucic acid gallates are selected from the group consisting of mucic acid 1,4-lactone 5-O-gallate, mucic acid 2-O-gallate, mucic acid 6-Methyl ester 2-O-gallate, mucic acid 1-Methyl ester 2-O-gallate and ellagic acid.

4. The method as in claim 1, wherein *Bacillus coagulans* strain is *Bacillus coagulans* MTCC 5856.

5. The method as in claim 1, wherein the effective dose of *Bacillus coagulans* is $1 \times 10^6$ to $1 \times 10^{14}$ colony forming units per unit dose.

6. The method as in claim 1, wherein the effective dose of *Bacillus coagulans* is $2 \times 10^9$ colony forming units per unit dose.

7. A method of therapeutic management of symptoms and infections of *Helicobacter pylori* strains in mammals, said method comprising administering a composition containing:
   a) at least 10% w/w 1-O-galloyl-β-D-glucose (β-glucogallin) and at least 10% w/w total mucic acid gallates, and
   b) an effective dose of probiotic bacteria *Bacillus coagulans*, to said mammals, to bring about a reduction in the symptoms and infections of *Helicobacter pylori*.

8. The method as in claim 7, wherein the strains of *H. pylori* include *Helicobacter pylori* ATCC 43504 and *Helicobacter pylori* ATCC 700392.

9. The method as in claim 7, wherein the mucic acid gallates are selected from the group consisting of mucic acid 1,4-lactone 5-O-gallate, mucic acid 2-O-gallate, mucic acid 6-Methyl ester 2-O-gallate, mucic acid 1-Methyl ester 2-O-gallate and ellagic acid.

10. The method as in claim 7, wherein the *Bacillus coagulans* strain is *Bacillus coagulans* MTCC 5856.

11. The method as in claim 7, wherein the effect dose of *Bacillus coagulans* is $1 \times 10^6$ to $1 \times 10^{14}$ colony forming units per unit dose.

12. The method as in claim 7, wherein the effective dose of *Bacillus coagulans* is $2 \times 10^9$ colony forming units per unit dose.

13. The method as in claim 7, wherein the symptoms of *H. pylori* infections are selected from the group consisting of gastritis, ache or burning pain in abdomen, nausea, loss of appetite, frequent burping, bloating, bad breath and unintentional weight loss.

14. The method as in claim 7, wherein infections of *H. pylori* strains are selected from the group consisting of epidemic gastritis, hypochlorhydria, gastroduodenal inflammation, ulcers, dyspepsia, gastric carcinoma and lymphoma, Gastroesophageal reflux disease and Extragastroduodenal disorders selected from the group consisting of coronary heart disease, dermatological disorders, rosacea, idiopathic urticaria, autoimmune thyroid disease and thrombocytopenic purpura, iron deficiency anemia, Raynaud's phenomenon, scleroderma, migraine, and Guillain-Barre' syndrome.

15. The method as in claim 7, wherein the composition is formulated with pharmaceutically/nutraceutically acceptable excipients, adjuvants, diluents or carriers and administered in the form of tablets, capsules, syrups, gummies, powders, suspensions, emulsions, chewables, candies and eatables.

16. The method as in claim 7, wherein the mammal is human.

* * * * *